United States Patent
Shimayama et al.

(10) Patent No.: US 7,626,597 B2
(45) Date of Patent: Dec. 1, 2009

(54) IMAGE DISPLAY METHOD, APPARATUS AND PROGRAM

(75) Inventors: Toshihide Shimayama, Kanagawa-ken (JP); Akira Hasegawa, San Jose, CA (US)

(73) Assignee: FUJIFILM Corporation, Tokyo (JP)

( * ) Notice: Subject to any disclaimer, the term of this patent is extended or adjusted under 35 U.S.C. 154(b) by 340 days.

(21) Appl. No.: 11/157,954

(22) Filed: Jun. 22, 2005

(65) Prior Publication Data

US 2005/0285812 A1 Dec. 29, 2005

(30) Foreign Application Priority Data

Jun. 23, 2004 (JP) .............................. 2004-184517

(51) Int. Cl.
*G09G 5/00* (2006.01)
(52) U.S. Cl. ....................... 345/634; 345/677; 715/732; 382/294
(58) Field of Classification Search ................. 345/474; 707/10
See application file for complete search history.

(56) References Cited

U.S. PATENT DOCUMENTS

| | | | | |
|---|---|---|---|---|
| 6,115,486 | A * | 9/2000 | Cantoni | 382/128 |
| 6,518,952 | B1 * | 2/2003 | Leiper | 345/156 |
| 6,574,629 | B1 * | 6/2003 | Kaufman et al. | 707/10 |
| 2002/0196249 | A1 * | 12/2002 | Peters et al. | 345/419 |
| 2003/0214290 | A1 * | 11/2003 | van Muiswinkel et al. | 324/307 |
| 2005/0084178 | A1 * | 4/2005 | Lure et al. | 382/294 |
| 2005/0232513 | A1 * | 10/2005 | Ritt et al. | 382/294 |
| 2006/0030769 | A1 * | 2/2006 | Ramamurthy et al. | 600/407 |

FOREIGN PATENT DOCUMENTS

| JP | 8-76741 A | 3/1996 |
|---|---|---|
| JP | 8-186762 A | 7/1996 |
| JP | 2002-158923 A | 5/2002 |

OTHER PUBLICATIONS

Title: "EAST Training for Examiners", Date: Aug. 1999, Edition: IS&R Version, p. 56.*

* cited by examiner

*Primary Examiner*—Hau H Nguyen
*Assistant Examiner*—David H Chu
(74) *Attorney, Agent, or Firm*—Sughrue Mion, PLLC (57) ABSTRACT

A method, apparatus and program for implementing the method is provided for performing efficient and stable comparative image observation in which a plurality of digital images inputted for comparative observation is switched and displayed on the screen of a display means. Brightness adjusting process for the plurality of images inputted for comparative observation, and aligning process for the structures of the subjects among the images are performed by the image processing means. Display control is implemented by the display control means such that each of the images is repeatedly switched and displayed on the screen of the display means at a favorable frame rate for comparative observation in the range from 1 to 5 fps based on the processed image data files.

19 Claims, 5 Drawing Sheets

IMAGE DISPLAY METHOD, APPARATUS AND PROGRAM

BACKGROUND OF THE INVENTION

1. Field of the Invention

The present invention relates to an image display method, apparatus and program for implementing the method. More specifically, the present invention is directed to an image display method, apparatus and program for implementing the method, in which a plurality of different images is displayed on a screen for comparative observation based on a plurality of image data files, each representing each of the different images.

2. Description of the Related Art

Comparative image observations are performed by simply placing the images side by side for those recorded on recording media, such as papers or films. In addition, if the recording media are films, they may be placed in a viewing box (Schaukasten) arranged side by side for comparison.

For digital images, several different image display methods for use in the comparative observation are proposed, as described, for example, in Japanese Unexamined Patent Publication Nos. 8(1996)-076741 and 8(1996)-186762. In the methods, images under comparative observation are displayed on the same screen of a display device, such as a CRT, LCD or the like, or each of the images is displayed on the respective screens of a plurality of different display devices arranged side by side.

Another type of image display method is also proposed as described, for example, in Japanese Unexamined Patent Publication No. 2002-158923. In the method, an image subtraction process (subtractive operation) is performed between the images to be used for comparative observation to generate a differential image that indicates the difference between the images, which is then used for observing the extracted difference.

The image display method that displays a plurality of images on the same screen, however, has the disadvantage that each of the images displayed on the screen is too small for accurate observation. On the other hand, the image display method in which respective images are displayed on the respective screens of a plurality of different display devices has the disadvantage that the entire display system becomes sizable, resulting in limited locations for installation and increased costs. In addition, both methods have another disadvantage in common that images are placed apart from each other in no small extent, so that the observer has to look at these images by shifting the visual axes, which is burdensome and exhausting for the observer.

The method using a differential image to observe the difference between the images has the disadvantage that the comparative image observation may sometimes become difficult simply because the differential image is a different image from either of the original images, making it difficult for the observer to correctly identify the subject of the image.

One promising idea which might be conceivable for avoiding these problems is a switch display method in which each of the images under comparative observation is switch and display on the screen of a single display device. Simple switching of the images, however, may result in faded memory of the previously displayed image if the switching time is relatively long, or it may result in double images to be observed which are superimposed on top of another due to the afterimage effect if the switching time is relatively short. Thus, the method also suffers from the problem that effective and stable comparative image observation is not provided with this method.

SUMMARY OF THE INVENTION

The present invention has been developed in view of the circumstances described above, and it is an object of the present invention to provide an image display method, apparatus and program for implementing the method that employs the switch display method, in which images under comparative observation are switched and displayed on the screen of the same display device, and yet allows an effective and stable comparative image observation.

The image display method of the present invention is an image display method for displaying a plurality of different images of the same type of subject used for a comparative observation on a screen of a single display means by switching the images, wherein the images are displayed repeatedly on the screen at a display rate in the range from 1 to 5 frames per second (fps).

The image display apparatus of the present invention comprises: a single display means having a screen for displaying images; and a display control means for controlling the display means such that a plurality of different images of the same type of subject is switched and displayed on the screen based on a plurality of image data files, each representing each of the different images, inputted for a comparative observation, wherein the display control means controls the display means such that the plurality of images is repeatedly displayed on the screen at a display rate in the range from 1 to 5 fps.

The image display apparatus of the present invention may further include an aligning means for substantially aligning the positions of subject structures among the plurality of images by performing image processing on at least one of the plurality of image data files to obtain a plurality of aligned image data files. In that case, the display control means may be adapted to implement the display control based on the plurality of aligned image data files.

The image display apparatus of the present invention may further include a display rate adjusting means for adjusting the display rate described above.

Preferably, the display rate of the apparatus of the present invention is in the range from 1.5 to 3.5 fps.

The plurality of images described above may be a plurality of images, each representing the same subject obtained at different times, a plurality of medical images, each representing the chest of the same human body obtained at different times, or two medical images of a pair of breasts, each representing either the left or right breast.

The program of the present invention is a program for causing a computer to perform a display control process for controlling a single display means having a screen such that a plurality of different images of the same type of subject is switched and displayed on the screen based on a plurality of image data files, each representing each of the different images, inputted for a comparative observation, wherein the display control process controls the display means such that the plurality of images is repeatedly displayed on the screen at a display rate in the range from 1 to 5 fps. The program of the present invention may be provided in the form of a computer program recorded on a computer readable recording medium.

The referent of "display rate" as used herein means a number of image frames to be switched and displayed in a predetermined time period, which is also known as the frame rate.

The image switching is not necessarily implemented at a constant display rate, and it may be varied temporarily or over time.

The referent of "repeatedly" as used herein means either repeating a number of predetermined times or until a terminating instruction is inputted.

The referent of "display means" as used herein means, for example, a CRT, LCD (liquid crystal display), PDP (plasma display panel), projector, or the like.

The referent of "image" as used herein means any type of digital image which may be used for a comparative observation. It may be, for example, a radiation image, tomographic (CT) image, or MRI image used for nondestructive inspection or medical diagnosis.

The specific range of values of the display rate described above is determined based on the evaluation tests conducted by the applicant in the following manner.

(Cases Used)

The evaluation tests were conducted using the following two different types of image sets.

1. Two simple chest x-ray images obtained at different times for the case where a nodular shadow of lung cancer is developing (Chest X-Ray).

2. Two mammograms obtained at different times for the case where a tumor shadow is developing (Mammogram).

(Evaluation Method)

Subjective visual evaluations were performed by displaying two images of the pair (Chest X-Ray or Mammogram) each time at a certain different frame rate. The point of evaluation was whether the difference between the two images in the abnormal shadow (nodular shadow or tumor shadow) was recognizable. The observer was the principal inventor.

(Evaluation Results)

The table 1 below summarizes the evaluation results.

TABLE 1

Evaluation Results

| Frames/sec. | Chest X-Ray | Mammogram |
| --- | --- | --- |
| 0.5 | too slow to recognize the difference | too slow to recognize the difference |
| 1 | recognizable, but too slow to clearly recognize the difference | recognizable, but too slow to clearly recognize the difference |
| 2 | clearly recognizable (best) | clearly recognizable |
| 3 | clearly recognizable | clearly recognizable (best) |
| 5 | too fast and tiring, difficult to recognize the difference | clearly recognizable |
| 10 | too fast and tiring, difficult to recognize the difference | too fast and tiring, difficult to recognize the difference |
| 20 | too fast to recognize the difference | too fast and tiring, difficult to recognize the difference |
| 100 | too fast to recognize the difference | too fast to recognize the difference |

(Conclusion)

The frame rates at which the difference is recognizable are 1, 2, 3 and 5 fps. Of these, 2 fps allows clear recognition of the difference for Chest X-Ray and 3 fps for Mammogram. Thus, the appropriate range of the frame rates may be from 1 to 5 fps, in particular, from 1.5 to 3.5 fps. The evaluation result may slightly vary dependent upon the dynamic vision of the observer and the accuracy of the image alignment, but the ballpark figures of the favorable rate for most of the observers may not deviate considerably from the range described above.

In the image display method, apparatus, and program for implementing the method of the present invention, the images used for comparison are repeatedly displayed on the screen of a single image display means at a rate in the range from 1 to 5 fps, which would be the range that allows each of the images visually observed remains memorized and yet identifiable, so that the difference among the images for comparison may be enhanced and the comparative image observation may be performed efficiently and stably.

Further, only a single image is displayed on the screen at a time, so that images may be displayed in relatively large size and the comparative image observation may be performed without shifting the visual axes of the observer. Still further, only a single display means is required instead of a plurality of display means, so that the costs may be kept low.

DESCRIPTION OF THE PREFERRED EMBODIMENTS

Hereinafter, embodiments of the present invention will be described with reference to the accompanying drawings.

Figure 1:
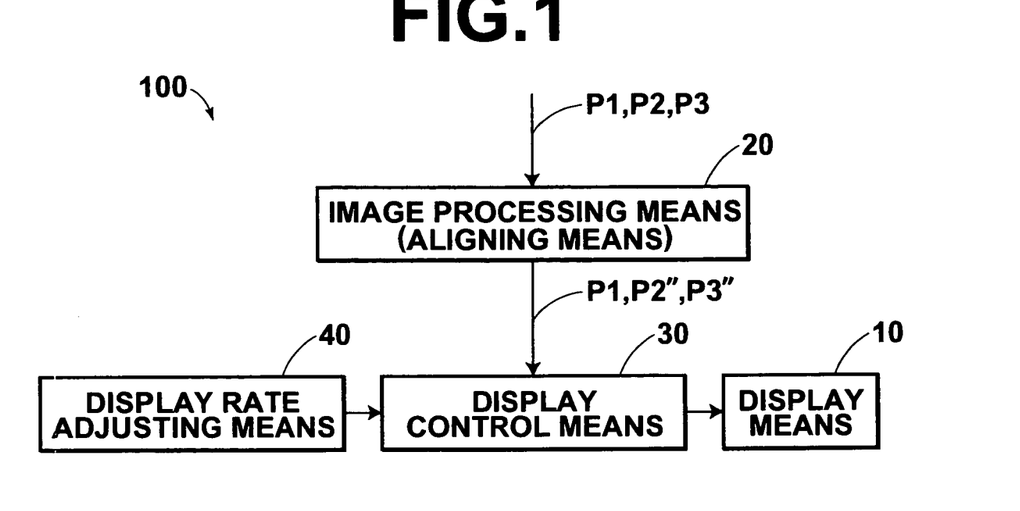
FIG. 1 is a schematic block diagram of an image display apparatus according to a first embodiment of the present invention, illustrating the configuration thereof.

FIG. 1 is a schematic block diagram of an image display apparatus 100, which is a first embodiment of an image display apparatus that employs an image display method of the present invention, illustrating the configuration thereof.

The image display apparatus 100 shown in FIG. 1 comprises: a single display means 10, such as a CRT, LCD, or the like; an image processing means 20 for performing image processing on at least one of a plurality of image data files inputted, each representing a chest x-ray image of the same patient obtained at different times, to substantially align the anatomical structures among the plurality of images; a display control means 30 for controlling the display means 10 such that the plurality of aligned chest x-ray images is repeatedly switched and displayed on the screen based on the plurality of the aligned image data files at a display rate at least in the range from 1 to 5 fps; and display rate adjusting means 40 for adjusting the display rate.

The image display apparatus 100 allows the observer to verify changes in the chest over time to determine if a lesion has been newly developed or to perform a follow-up diagnosis of a lesion already developed by observing the chest x-ray images displayed on the apparatus.

Hereinafter, the operation of the image display apparatus 100 will be described.

Figure 2:
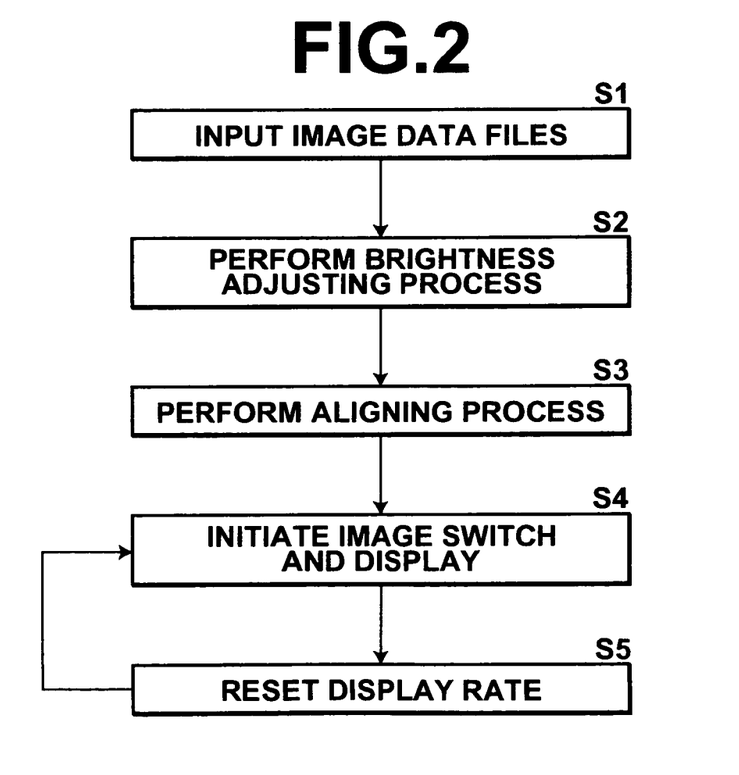
FIG. 2 is a drawing illustrating the process flow of the image display apparatus according to the first embodiment of the present invention.

FIG. 2 shows a schematic process flow of the image display apparatus 100.

Figure 3A:
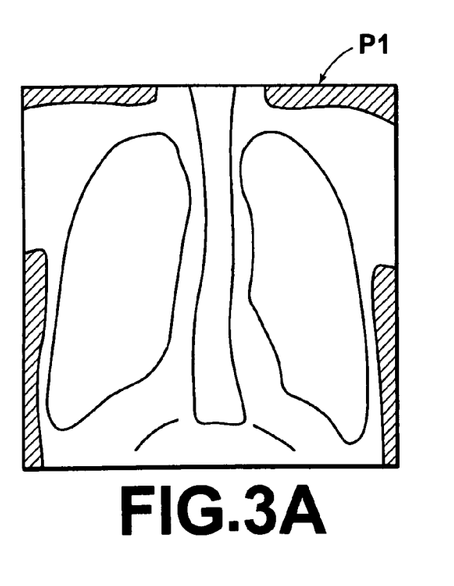
FIGS. 3A to 3C are drawings illustrating a plurality of chest x-rays arranged in chronological order.
Figure 3B:
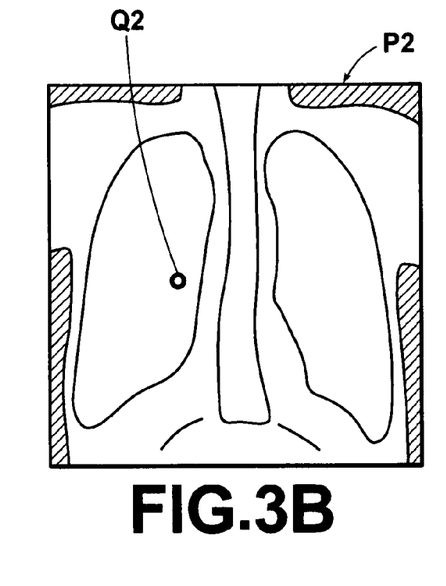
Figure 3C:
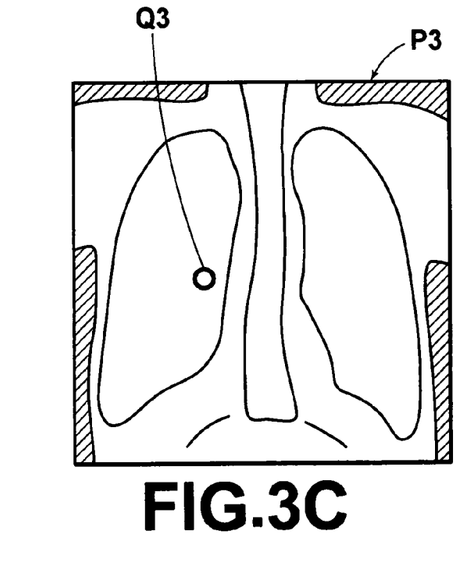

For example, image data files P1, P2 and P3, each representing each of the three chest x-ray images P1, P2 and P3 (same reference numeral is used for both the image data file and image represented by the image data file for convenience) of the same patient obtained at different times shown in FIG. 3 are read out from an image database or the like (not shown) and inputted to the image display apparatus 100 (step S1). These image data files may be obtained, for example, by the Computed Radiography System (CR System) or the like. Q2 and Q3 shown in the drawing indicate changes over time in the affected portion, such as a tumor mass.

When the image data files P1, P2 and P3 are inputted to the apparatus, the image processing means 20 initially performs brightness adjustment on each of the image data files so that the chest x-ray images P1, P2 and P3 represented by the image data files have substantially an identical brightness level (step S2). If this step is omitted and each of the chest x-ray images has a different brightness level, recognition errors may occur for the structures of the chest in each of the images in performing the aligning operation to be described later, or images displayed on the apparatus may become less favorable to the observer. Specifically, the brightness levels may be adjusted, for example, by the two methods described below.

1) Maximum and Minimum Pixel Value Matching Method

Two sets of pixel values (each representing the brightness) of first and second images are defined here as S1 and S2 respectively. A maximum value Max1 and a minimum value Min1 of the set S1, and a maximum value Max2 and a minimum value Min2 of the set S2 are calculated according to the Formulae (1) to (4) shown below.

$$\text{Max1} = \underset{p \in S1}{\text{Max}}(p) \quad (1)$$

$$\text{Min1} = \underset{p \in S1}{\text{Min}}(p) \quad (2)$$

$$\text{Max2} = \underset{p \in S2}{\text{Max}}(p) \quad (3)$$

$$\text{Min2} = \underset{p \in S2}{\text{Min}}(p) \quad (4)$$

Then, with reference to the first image (S1), each pixel value p of the second image (S2) is converted to p' according to the Formula 5 shown below to match the brightness between the two images.

$$P' = \frac{\text{Max1} - \text{Min1}}{\text{Max2} - \text{Min2}} \times (p - \text{Min2}) + \text{Min1} \quad (5)$$

2) Averaged Pixel Value/Variance Matching Method

Two sets of pixel values of first and second images are defined here as S1 and S2 respectively. Assuming the number of pixels as N, an averaged pixel value $\mu 1$ and a variance ($\delta 1 \times \delta 1$) of the S1, and an averaged pixel value $\mu 2$ and a variance ($\delta 2 \times \delta 1$) of the S2 are calculated according to the Formulae (6) to (9) shown below.

$$\mu 1 = \frac{1}{N} \sum_{p \in S1} p \quad (6)$$

$$\delta 1^2 = \frac{1}{N} \sum_{p \in S1} (p - \mu 1)^2 \quad (7)$$

$$\mu 2 = \frac{1}{N} \sum_{p \in S2} p \quad (8)$$

$$\delta 2^2 = \frac{1}{N} \sum_{p \in S2} (p - \mu 2)^2 \quad (9)$$

Then, with reference to the first image (S1), each pixel value p of the second image (S2) is converted to p' according to the Formula 10 shown below to match the brightness between the two images.

$$p' = \frac{\delta 1}{\delta 2}(p - \mu 2) + \mu 1 \quad (10)$$

Here, it is assumed that the brightness of the image P2 and P3 is adjusted with reference to the brightness of the image P1 according to one of the methods described above.

Next, the aligning process is performed on each of the image data files P1, P'2, and P'3 such that the anatomical structures of the chest on the chest x-ray images represented by the image data files P1, P'2, and P'3 are matched substantially with each other (step S3). As for the aligning method, the following methods may be used.

With one of the three images defined as the reference image, an overall aligning operation, such as translation, rotation, or scaling (linear alignment using affine transformation or the like), is performed between the two images in each pair of the reference image and one of the other two images. Then, regions of interest (template regions), which are multitudes of small regions, are set on one of the two images having been aligned broadly, and search regions, each corresponding to each template region and having larger size than the template region are set on the other. For each pair consisting of each template region and corresponding search region, a partial region that substantially corresponds to the template region (template corresponding region) within the search region is obtained. Then, based on the relative position between each template region on one of the images and the template corresponding region on the other, an amount of shift for matching each template region with each template corresponding region is calculated. Based on the calculated amount of shift, nonlinear transformation (warping) is performed through curve fitting (e.g., two-dimensional $n^{th}$-order polynomial, $n \geq 2$) for the two images having been aligned broadly.

In addition, another image aligning method is proposed by the applicant as disclosed in Japanese Unexamined Patent Application Nos. 2001-325584 and 2002-324238. The method uses an image in which a certain structure is emphasized to perform aligning operation between the images such that the emphasized structures match with each other. By using images in which a bony or soft tissue portion is emphasized, the method may provide broadly aligned images in the bony or soft tissue portion.

A further image aligning method is proposed by the applicant as disclosed in Japanese Unexamined Patent Publication No. 2002-324238. In the method, a desired portion, bony or soft tissue portion, is emphasized to broadly align the images in the emphasized portion. Then, using the broadly aligned images, a local aligning operation is performed between the images. According to the two-stage aligning method, two images are aligned relatively well depending on the intended use.

Here, it is assumed that the aligning operation is performed on the images P'2 and P'3 with reference to the image P1 to obtain aligned image data files P1, P''2 and P''3 according to one of the methods described above.

After the aligned image data files are obtained, the display control means 30 initiates the switch display for the chest x-ray images when triggered, for example, by a signal input that instructs initiation of the switch display. That is, based on the image data files P1, P''2 and P'''3 which have been adjusted in the brightness and aligned in the anatomical structures, the display control means 30 controls the display means 10 such that the chest x-ray images P1, P''2 and P'''3, each represented by each of the image data files, are repeatedly switched and displayed on the screen of the display means 10 at a predetermined display rate of around 1.5 to 3.5 fps.

The display rate adjusting means 40 resets the display rate prior to or during the switch display based on the information inputted through, for example, an input means, such as a key board, mouse, hardware device having a button or dial, or the like (not shown) (step S5). This allows the operator to adjust the switch display at a desired rate which is favorable to the operator.

The switch display of the images is terminated, for example, after a predetermined time has elapsed, or the termination is triggered when a signal that instructs the termination is inputted. Alternatively, the switch display may be continued only while a signal input instructing the switch display is maintained.

Through the switch display described above, the difference among each of the images, for example, the distinctive area Q2 or Q3 that indicates a tumor or the like on the images P1 through P3 may stands out clearly.

Figure 4:
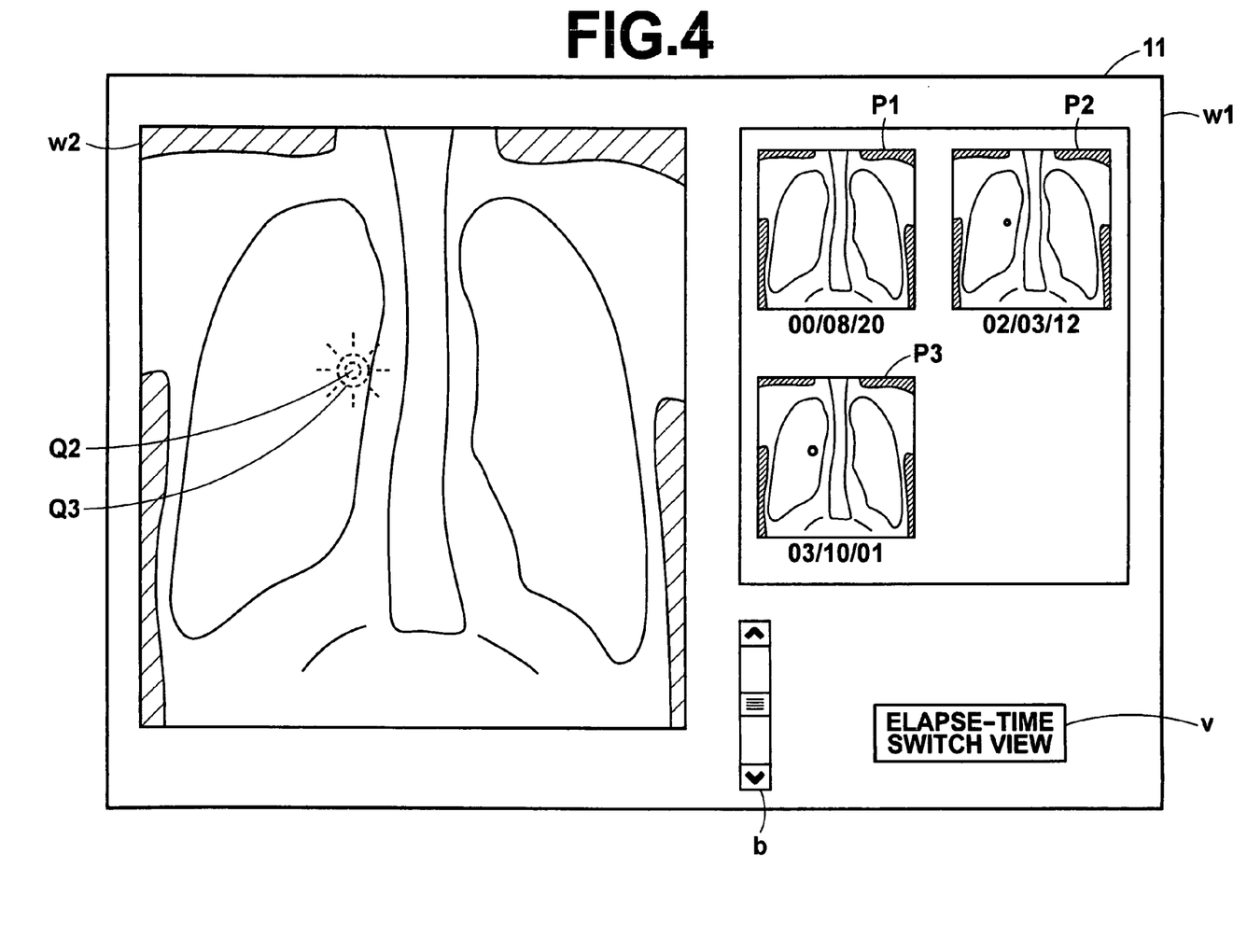
FIG. 4 is a drawing illustrating an example layout of the screen of the display means according to the first embodiment.

FIG. 4 is a drawing illustrating an example layout of the screen 11 of the display means 10 according to the first embodiment of the present invention described above. The screen 11 has a window w1 in which reduced images of the inputted images are displayed in the order in which they were obtained, so that the operator may select desired images to be used for the switch display. In addition to the window w1, the screen 11 has a switch display region w2. The size of the switch display region w2 is variable, and it may be extended to full screen or displayed on a portion of the screen. The screen 11 further shows an "elapse-time switch view" button v for inputting a trigger signal to instruct initiation/termination of the switch display, and a scroll bar b for adjusting the display rate. The operator may initiate/terminate the switch display by pressing the button v with a pointer on the screen through a mouse or the like, and may adjust the display rate by sliding the position of the button of the scroll bar b.

In the present embodiment, the display rate is set through the scroll bar displayed on the screen of the display means 10. Alternatively, for example, a rotating hardware device such as a dial may be used to set the display rate according to the rotational position or amount.

Further, the display rate may be varied such that the images are switched rapidly at the beginning and then gradually switched more slowly, as well as maintained constant. For example, initially the display rate may be set at 5 fps, then gradually slowed down to 0.5 fps (1 frame every 2 seconds) after 10 seconds have elapsed. By doing so, the operator may roughly confirm the difference among the images during the rapid switching period, and then identify the exact location of the differing area causing the difference in each of the images (e.g., position relative to the normal tissue, or the like) during the slow switching period.

Figure 5:
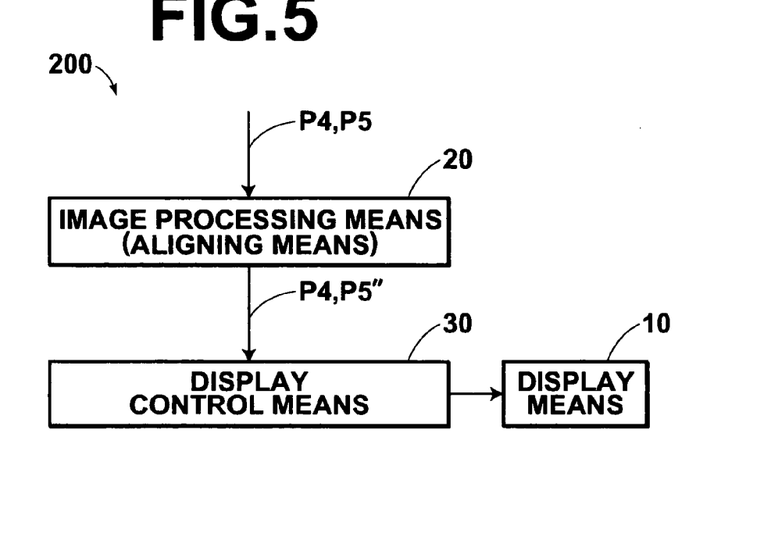
FIG. 5 is a schematic block diagram of an image display apparatus according to a second embodiment of the present invention, illustrating the configuration thereof.

FIG. 5 is a schematic block diagram of an image display apparatus 200, which is a second embodiment of an image display apparatus that employs an image display method of the present invention, illustrating the configuration thereof. The image display apparatus 200 shown in FIG. 5 comprises: a display means 10; an image processing means 20 for performing image processing on at least either of two image data files inputted therein, each representing a mammogram of either the left or right breast of the same patient (medical x-ray image of breast), to substantially align the anatomical structures between the two images; a display control means 30 for controlling the display means 10 to display the two aligned mammograms on the screen based on the two aligned image data files, in which the mammograms are switched once and the switched mammogram is displayed on the screen in response to a switching signal inputted from an input means (not shown) instructing the switching of the mammograms. Thus, each of the two mammograms may be repeatedly switched and displayed on the screen at a display rate in the range from 1 to 5 fps when the switching signal is inputted continuously.

The image display apparatus 200 allows the observer to perform a medical diagnosis, including determination of a lesion, through verification of an asymmetrical portion of the right and left breasts by observing the mammograms displayed on the screen.

Hereinafter, the operation of the image display apparatus 200 will be described.

Figure 6:
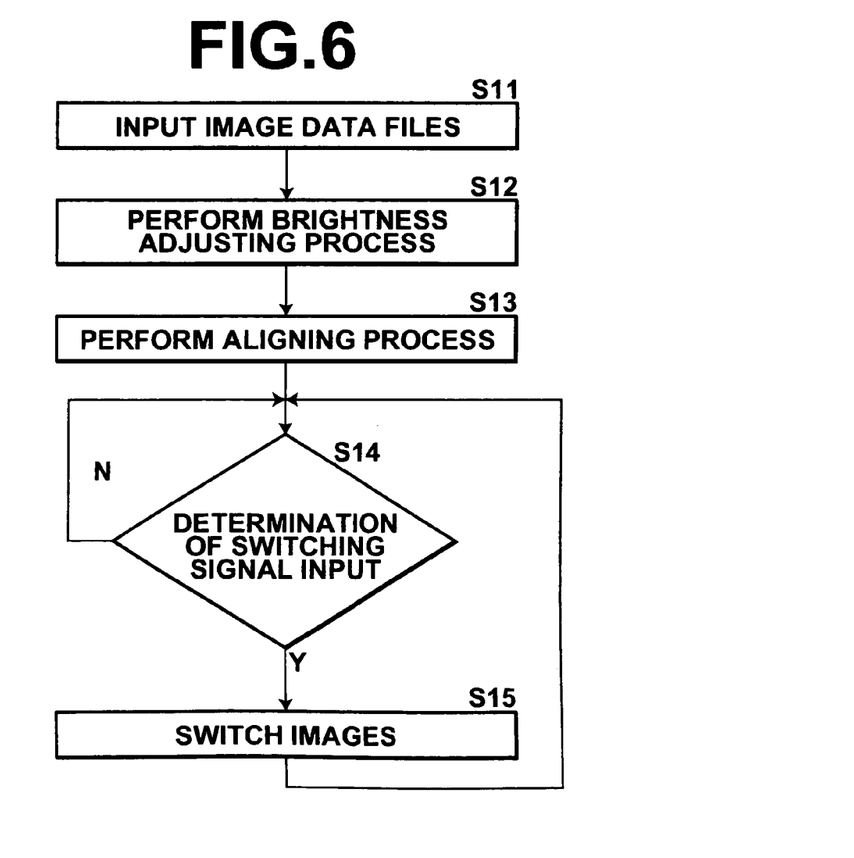
FIG. 6 is a drawing illustrating the process flow of the image display apparatus according to the second embodiment of the present invention.

FIG. 6 is a drawing schematically illustrating the process flow of the image display apparatus 200.

Figure 7A:
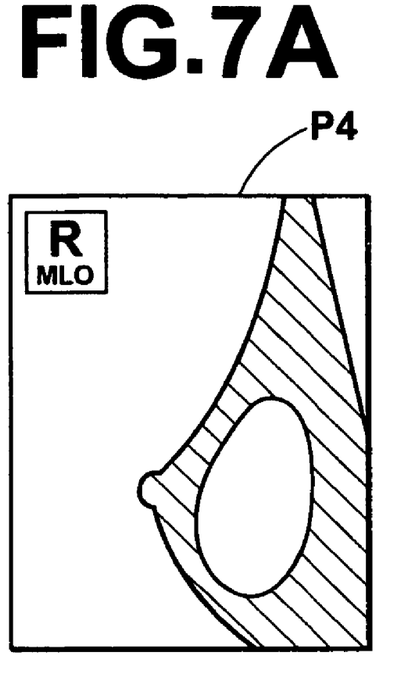
FIGS. 7A and 7B are drawings illustrating mammograms of a pair of right and left breasts.
Figure 7B:
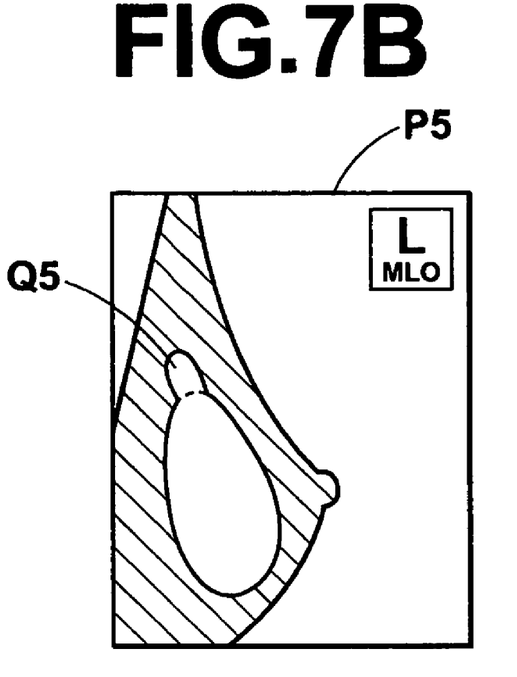

For example, image data files P4 and P5, each representing each of mammograms P4 and P5 of the right and left breasts of the same patient shown in FIG. 7 are inputted to the image display apparatus 200 (step S11). Q5 in the FIG. 7 indicates an asymmetrical portion between the right and left breasts.

When the image data files P4 and P5 are inputted to the apparatus, the image processing means 20 performs brightness adjustment on each of the image data files through the identical method as in the first embodiment (step S12) to obtain image data files P4 and P'5, and then aligning operation (step S13) to obtain image data files P4 and P'''5.

As for the image aligning method for mammograms, it is of course possible to apply the method used in the first embodiment. In this case, however, a more simple method may be applied as described, for example, in Japanese Unexamined Patent Publication No. 2002-65613. In the method, the position of the breast in each of the images is identified by a known recognition method, and warping process is performed on either of the images such that the positions of the image edge on the side of the breast muscle and nipple are matched respectively between the two images.

Generally, on mammograms that represent the right and left breasts respectively, the orientation of the breasts are indicated symmetrically, so that either of the images is flipped left to right when aligning.

After aligned image data files are obtained, the display control means 30 displays, for example, either of the image P4 or P'''5 on the screen of the display means 10, and waits for a switching signal to be inputted (step S14).

Here, when a switching signal is inputted by the operator through pressing a predetermined button of an input means, such as a key board or mouse (not shown), the display control means 30 switches the mammogram to be displayed to the other only once in response to the switching signal (step S15).

This means that the mammogram displayed on the screen may be switched every time the switching signal is inputted by the operator. Thus, if the switching signal is inputted repeatedly by the operator at predetermined timings, the mammograms, each representing either the left or right breast, may be alternately switched and displayed on the screen. The display rate may be varied at will by changing the timings of inputting the switching signal, so that switching signal may readily be halted temporarily to interrupt the image switching in the middle of the comparative observation and to observe one of the mammograms carefully, as well as adjusting the display rate.

Such switch display may cause only an asymmetrical portion, such as the asymmetrical portion Q5, to stand out clearly. The operator may perform diagnosis for breast cancer or the like by discovering such an asymmetrical portion and observing the portion in more detail.

Thus, according to the first and second embodiment of the present invention, each of the images for comparison is repeatedly displayed on the screen of a single image display means at a rate in the range from 1 to 5 fps, which would be the range that allows each of the images visually observed remains memorized and yet identifiable, so that the difference among the images for comparison may be enhanced and the comparative image observation may be performed efficiently and stably.

Further, only a single image is displayed on the screen at a time, so that images may be displayed in relatively large size and the comparative image observation may be performed without shifting the visual axes of the observer. Still further, only a single display means is required instead of a plurality of display means, so that the costs may be kept low.

If the images for comparative observation are mammograms, they are not limited to the left and right breasts obtained at the same time, but may be those obtained at different times for different breasts (left or right). For example, they may be a mammogram of the right breast obtained currently and a mammogram of the left breast obtained in the past, or they may be the same breast obtained at different times as in the chest x-ray images. Observation of the images of the same breast obtained at different times allows ease of checking for the development of calcification over time which is characteristic of breast cancer.

The switch display may be such that each of the images is completely switched over, or either of the images is superimposed on top of another as a translucent image.

What is claimed is:

1. An image display method comprising:
   aligning positions of a same type of subject present in a plurality of different images by performing image processing on at least one of a plurality of image data files corresponding to the plurality of the different images to obtain a plurality of aligned image data files;
   displaying the plurality of different images corresponding to the obtained plurality of the aligned image data files of the same type of subject for a comparative observation on a screen of a single display means by switching the images; and
   adjusting display rates on the single display means,
   wherein the images are displayed repeatedly on the screen at a display rate in the range from 1 to 5 fps,
   wherein the adjusting comprises adjusting the display rate only between 1 to 5 fps when displaying the plurality of the different images.

2. An image display apparatus, comprising:
   a single display means having a screen for displaying images;
   an aligning means for substantially aligning positions of a same type of subject present in a plurality of different images by performing image processing on at least one of a plurality of image data files corresponding to the plurality of the different images to obtain a plurality of aligned image data files;
   a display control means for controlling the display means such that the plurality of different images of the same type of subject are switched and displayed on the screen based on the obtained plurality of the aligned image data files for a comparative observation; and
   a display rate adjusting means for adjusting display rates on the single display means,
   wherein the display control means controls the display means such that the plurality of different images are repeatedly displayed on the screen at a display rate in the range from 1 to 5 fps,
   wherein the display rate adjusting means adjusts the display rate only between 1 to 5 fps when displaying the plurality of the different images.

3. The image display apparatus according to claim 2, wherein the display rate is in the range from 1.5 to 3.5 fps.

4. The image display apparatus according to claim 2, wherein the plurality of images is a plurality of images, each representing the same subject, obtained at different times.

5. The image display apparatus according to claim 2, wherein the plurality of images is a plurality of medical images, each representing the chest of the same human body, obtained at different times.

6. The image display apparatus according to claim 2, wherein the plurality of images is two medical images of a pair of breasts, each representing either the left or right breast, obtained at different times.

7. A computer-readable storage medium storing thereon a program for causing a computer to perform a display control method comprising:
   aligning positions of a same type of subject present in a plurality of different images by performing image processing on at least one of a plurality of image data files corresponding to the plurality of the different images to obtain a plurality of aligned image data files;
   controlling a single display means having a screen such that the plurality of different images of the same type of subject are switched and displayed on the screen based on the obtained plurality of the aligned image data files for a comparative observation; and
   adjusting display rates on the single display means,
   wherein the controlling comprises controlling the display means such that the plurality of images are repeatedly displayed on the screen at a display rate in the range from 1 to 5 fps,
   wherein the adjusting comprises adjusting the display rate only between 1 to 5 fps when displaying the plurality of the different images.

8. The image display method according to claim 1, wherein the image processing is performed on the at least one of the plurality of image data files with reference to at least one other image data file among the plurality of image data files to align the subject of the at least one of the plurality of image data files to the same type of the subject of the at least one other image data file among the plurality of image data files.

9. The image display apparatus according to claim 2, wherein the aligning means performs the image processing on the at least one of the plurality of image data files with reference to at least one other image data file among the plurality of image data files to align the subject of the at least one of the plurality of image data files to the same type of the subject of the at least one other image data file among the plurality of image data files.

10. The computer-readable storage medium according to claim 7, wherein the image processing is performed on the at least one of the plurality of image data files with reference to at least one other image data file among the plurality of image data files to align the subject of the at least one of the plurality of image data files to the same type of the subject of the at least one other image data file among the plurality of image data files.

11. The image display method of claim 8, wherein the displaying the plurality of the different images comprises displaying, sequentially in time, the plurality of the different images corresponding to the obtained plurality of the aligned image data files on the screen of the single display means at the display rate in the rage from 1 to 5 fps.

12. The image display method of claim 11, wherein the displaying the plurality of the different images sequentially in time comprises individually displaying, in sequence, the plurality of the different images corresponding to the obtained plurality of the aligned image data files.

13. The image display method of claim 11, wherein the plurality of the different images are displayed sequentially in time for the comparative observation between the same type of subject of the plurality of the different images corresponding to the obtained plurality of the aligned image data files.

14. The image display apparatus of claim 9, wherein the display control means controls the display means such that the plurality of the different images corresponding to the obtained plurality of the aligned image data files are displayed, sequentially in time, on the screen of the single display means at the display rate in the rage from 1 to 5 fps.

15. The image display apparatus of claim 14, wherein the display control means controls the display means such that the plurality of the different images corresponding to the obtained plurality of the aligned image data files are displayed individually in sequence.

16. The image display apparatus of claim 14, wherein the display control means controls the display means such that the plurality of the different images are displayed sequentially in time for the comparative observation between the same type of subject of the plurality of the different images corresponding to the obtained plurality of the aligned image data files.

17. The computer-readable storage medium according to claim 10, wherein the displaying the plurality of the different images comprises displaying, sequentially in time, the plurality of the different images corresponding to the obtained plurality of the aligned image data files on the screen of the single display means at the display rate in the rage from 1 to 5 fps.

18. The computer-readable storage medium of claim 17, wherein the displaying the plurality of the different images sequentially in time comprises individually displaying, in sequence, the plurality of the different images corresponding to the obtained plurality of the aligned image data files.

19. The computer-readable storage medium of claim 17, wherein the plurality of the different images corresponding to the obtained plurality of the aligned image data are displayed sequentially in time for the comparative observation between the same type of subject of the plurality of the different images corresponding to the obtained plurality of the aligned image data files.

* * * * *